US012005268B2

(12) United States Patent
MacKenzie

(10) Patent No.: US 12,005,268 B2
(45) Date of Patent: Jun. 11, 2024

(54) OCULAR LIGHT THERAPY ARRANGEMENT AND METHOD FOR TREATING NEUROLOGICAL DISORDERS

(71) Applicant: Norb Lighting, LLC., Nunica, MI (US)

(72) Inventor: David S. MacKenzie, Nunica, MI (US)

(73) Assignee: Norb Lighting, LLC, Nunica, MI (US)

( * ) Notice: Subject to any disclaimer, the term of this patent is extended or adjusted under 35 U.S.C. 154(b) by 0 days.

(21) Appl. No.: 17/303,318

(22) Filed: May 26, 2021

(65) Prior Publication Data

US 2021/0370091 A1 Dec. 2, 2021

Related U.S. Application Data

(60) Provisional application No. 63/030,595, filed on May 27, 2020.

(51) Int. Cl.
*A61N 5/06* (2006.01)

(52) U.S. Cl.
CPC .... *A61N 5/0622* (2013.01); *A61N 2005/0632* (2013.01); *A61N 2005/0648* (2013.01); *A61N 2005/0651* (2013.01); *A61N 2005/0658* (2013.01)

(58) Field of Classification Search
CPC .......... A61N 5/0622; A61N 2005/0632; A61N 2005/0648; A61N 2005/0651; A61N 2005/0658; A61N 2005/0662
See application file for complete search history.

(56) References Cited

U.S. PATENT DOCUMENTS

| | | | |
|---|---|---|---|
| 4,940,323 A * | 7/1990 | Downing | A61N 5/06 351/203 |
| 5,447,527 A | 9/1995 | Waldman | |
| 5,530,628 A | 6/1996 | Ngai | |
| 5,690,421 A | 11/1997 | Shea et al. | |
| 6,350,275 B1 | 2/2002 | Vreman | |
| 7,883,534 B1 | 2/2011 | Crosby | |
| 10,806,890 B2 | 10/2020 | Burstein | |
| 2002/0029071 A1 | 3/2002 | Whitehurst | |
| 2003/0223036 A1 | 12/2003 | Anderson et al. | |
| 2006/0077662 A1 | 4/2006 | Dean et al. | |

(Continued)

FOREIGN PATENT DOCUMENTS

| | | |
|---|---|---|
| JP | 64-063201 | 3/1989 |
| KR | 102013809 B1 * | 8/2019 |

(Continued)

OTHER PUBLICATIONS

Noseda et al., Migraine Photophobia Originating in Cone-Driven Retinal Pathways. Brain: A Journal of Neurology. 2016; 1-16.

(Continued)

*Primary Examiner* — Carl H Layno
*Assistant Examiner* — Aya Ziad Bakkar
(74) *Attorney, Agent, or Firm* — Price Heneveld LLP

(57) ABSTRACT

An ocular light therapy arrangement for treating a user having a neurologic disorder includes a light emitting device the emits a light having a flicker rate of less than or equal to about 2 Hz and/or greater than or equal to about 85,000 Hz at a wavelength of within a first range of from about 500 nm to about 565 nm, wherein the light is effective to reduce neurologic disorder symptoms by reducing stimulation of the user's retina and brain cortex.

21 Claims, 1 Drawing Sheet

(56) References Cited

U.S. PATENT DOCUMENTS

| | | |
|---|---|---|
| 2006/0125418 A1 | 6/2006 | Bourgault |
| 2006/0158090 A1 | 7/2006 | Wang et al. |
| 2006/0262272 A1 | 11/2006 | Anderson |
| 2009/0005837 A1* | 1/2009 | Olmstead ............ A61N 5/0618 607/88 |
| 2009/0222070 A1 | 9/2009 | Daffer |
| 2012/0041520 A1 | 2/2012 | Colbaugh |
| 2013/0053929 A1 | 2/2013 | Colbaugh |
| 2019/0209806 A1* | 7/2019 | Allen ................ A61M 21/0094 |

FOREIGN PATENT DOCUMENTS

| | | | | |
|---|---|---|---|---|
| WO | WO-2017097708 A1 * | 6/2017 | ........... | A61N 5/0618 |
| WO | WO-2018152255 A1 * | 8/2018 | ............ | A61M 21/00 |

OTHER PUBLICATIONS

U.S. Commisioner for Patents; International Search Report and Written Opinion for Application No. PCT/US2016/38107; dated Oct. 19, 2016; entire document.

Linda Chalker-Scott; Basic Environmental Photobiology; Washington State University Puyallup Research and Extension Center, 2606 W. Pioneer, Puyallup, WA 98371.

Durand et al; Sunfleck properties from time series of fluctuating light; Agricultural and Forest Meteorology; 2021; 308-309; Elsevier Publishing Company; Amsterdam, Netherlands.

* cited by examiner

OCULAR LIGHT THERAPY ARRANGEMENT AND METHOD FOR TREATING NEUROLOGICAL DISORDERS

CROSS-REFERENCE TO RELATED APPLICATIONS

This application claims the benefit of U.S. Provisional Patent Application No. 63/030,595, entitled OCULAR LIGHT THERAPY ARRANGEMENT AND METHOD FOR TREATING NEUROLOGICAL DISORDERS, filed on May 27, 2020, the entire disclosure of which is incorporated herein by reference.

BACKGROUND

The aspects as disclosed and described herein relate to an ocular light therapy arrangement and method for utilizing the same, and in particular to an ocular light therapy arrangement and method for treating a user having a neurological disorder, such as migraines, fibromyalgia, neuropathy, chronic headaches, and the like.

BRIEF SUMMARY

One aspect includes an ocular light therapy arrangement for treating a user having a neurologic disorder, the arrangement including a light emitting device that emits a light having a flicker rate of less than or equal to about 2 Hz and/or greater than or equal to about 85,000 Hz at a wavelength of within a first range of from about 500 nm to about 565 nm, wherein the light is effective to reduce neurologic disorder symptoms by reducing stimulation of the user's retina and brain cortex relative to other frequencies of light.

Another aspect includes a method for treating a neurological disorder of a user with an ocular light therapy arrangement that includes providing a light emitting device, actuating the light emitting device such that the light emitting device produces a light having a flicker rate of less than or equal to about 2 Hz and/or greater than or equal to about 85,000 Hz at a wavelength of within a first range of from about 500 nm to about 565 nm, and positioning the light emitting device such that the light emitted from the light emitting device illuminates a space occupied by the user, wherein the light is effective to reduce neurologic disorder symptoms by reducing stimulation of the user's retina, thalamus and brain cortex relative to other frequencies of light.

Yet another aspect includes an ocular light therapy arrangement for treating a user having a neurologic disorder, the arrangement including a light emitting device that emits a light having a flicker index of less than or equal to about 2.0 at a wavelength of within a first range of from about 500 nm to about 565 nm, wherein the light is effective to reduce neurologic disorder symptoms by reducing stimulation of the user's retina, thalamus and brain cortex relative to other light frequencies.

The present inventive ocular light therapy arrangement and method is effective for treating users having a neurological disorder, and in particular to reducing the neurological disorder symptoms typically associated with neurological disorders such as migraines, fibromyalgia, neuropathy, chronic headaches, and the like, and provides a relatively low cost treatment for such disorders eliminating or reducing the necessity for medications and, in turn, side effects typically associated with such drugs and medications, eliminating or reducing the necessity for invasive procedures and the side effects and serious risk factors associated therewith, and is particularly well adapted for the proposed use. As a result, the present inventive arrangement and related method may allow the user to resume or conduct normal indoor life/work functions and activities without having to seek refuge and/or recovery in a separate dark or dimly lit room.

These and other features, advantages, and objects of the embodiments as disclosed herein will be further understood and appreciated by those skilled in the art by reference to the following specification, claims, and appended drawings.

DETAILED DESCRIPTION

Figure 1:
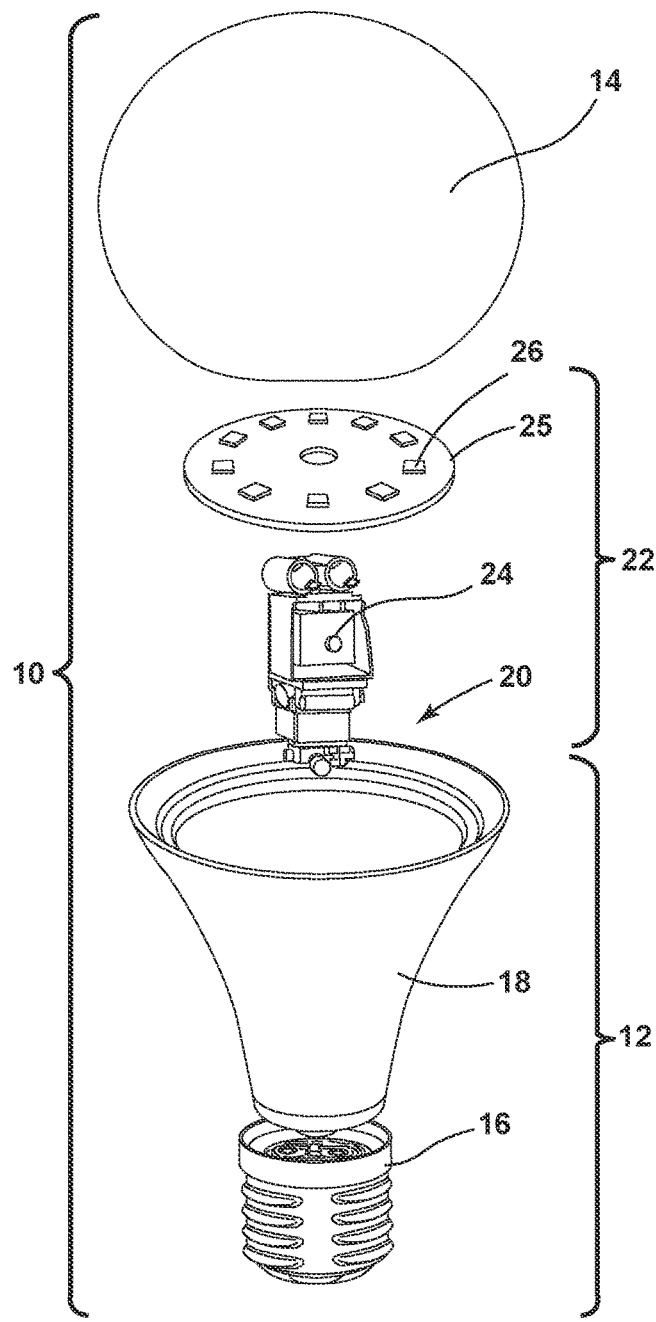
FIG. 1 is an exploded perspective view of an ocular light therapy arrangement.

For purposes of description herein, the terms "upper," "lower," "right," "left," "rear," "front," "vertical," "horizontal," and derivatives thereof shall relate to the invention as oriented in FIG. 1. However, it is to be understood that the invention may assume various alternative orientations, except where expressly specified to the contrary. It is also to be understood that the specific devices and processes illustrated in the attached drawings, and described in the following specification are simply exemplary embodiments of the inventive concepts defined in the appended claims. Hence, specific dimensions and other characteristics relating to the embodiments disclosed herein are not to be considered as limiting, unless the claims expressly state otherwise.

The reference numeral 10 (FIG. 1) generally represents an ocular light therapy arrangement as disclosed and described herein. In the illustrated example, the ocular light therapy arrangement includes a light emitting device, and in particular, may include a light emitting diode (LED) light bulb. In the illustrated example, the light bulb 10 includes a base assembly 12 and a light diffuser 14, where the base assembly 12 includes a base member 16 and a housing 18, the housing 18 cooperating with the diffuser 14 to form an interior space 20. The light bulb 10 may further include an LED arrangement 22 located within the interior space 20 where the LED arrangement 22 includes an LED driver 24 and an LED array 25 including one or more LEDs 26.

In the illustrated example, the base member 16 includes a standard E26 threaded bulb connector, however, other configurations of the base member 16 may be utilized depending upon the application and connection requirements for the overall light bulb 10.

The LED arrangement 22 is configured such that the light bulb emits a light configured to treat neurological disorders. Specifically, the light as emitted from the light bulb 10 is configured to reduce stimulation of the retina and the brain cortex of a user, thereby reducing or eliminating neurological disorder symptoms associated with neurological disorders, such as migraines, fibromyalgia, neuropathy, chronic headaches, and the like.

In the illustrated example, the light bulb 10 is configured to produce a non-flickering light, preferably wherein the majority of the light emitted is within a narrow band green light spectrum or within the range of from about 500 nm to about 565 nm, more preferably within the range of between 500 nm and 565 nm, even more preferably within the range of between about 510 nm and about 550 nm, and most preferably where the wavelength is about 525 nm. The light bulb 10 may further be configured such that the light as emitted has a flicker rate of preferably less than or equal to about 2 Hz, more preferably of less than or equal to about 1 Hz, and most preferably of about zero Hz. The light bulb 10 may also be configured such that the light as emitted has a flicker rate of greater than or equal to about 85,000 Hz in addition to as an alternative to the light as emitted at the lower flicker rate as described above. The light bulb 10 may also be configured such that the emitted light is entirely between a wavelength range of about 480 nm to about 600 nm. Still further, the light bulb 10 may be configured to have an output of between about 1 lumen and about 1000 lumen, wherein more preferably the output of the light bulb 10 is variable between about 300 lumen and about 600 lumen such that a user can vary the overall intensity of the light as emitted from the light bulb 10. In one example, the light emitting device is configured to have an output of greater than or equal to about 600 lumen.

The light bulb 10 may further be configured such that the flicker index of the light as emitted from the light bulb 10 is preferably less than or equal to about 2.0, more preferably is less than or equal to about 1.0, and most preferably is less than about 0.02, where the flicker index is a measure of the cyclic variation in output of the light source, taking into account the waveform of the light output, and is specifically the ratio of the area under the light output curve that is above the average light output level to the total area under the light output curve for a single cycle. Still further, the light bulb 10 may be configured such that the light as emitted from the light bulb 10 preferably has less than or equal to about 6% flicker, more preferably of less than or equal to about 5% flicker, and most preferably of less than or equal to about 2.5%, where the flicker percentage is the measure of the maximum light versus the minimum light in the cycle, and accounts for the minimum and maximum light outputs without differentiating between waveforms.

The light bulb 10 may further be configured such that the light as emitted from the light bulb 10 is emitted at a second wavelength in addition to the wavelengths as described above, and in particular at a wavelength within the infrared wavelength range. Specifically, the LED light bulb 10 may be configured such that the light as emitted from the light bulb 10 is additionally within a wavelength range preferably of between about 700 nm and about 1 mm, more preferably within a range of 700 nm to 1 nm, and most preferably within a range of about 710 nm to about 850 nm. It is noted that the combination of the two wavelength ranges, namely, the wavelength ranges within the range of between about 500 nm to about 565 nm and between about 700 nm and 1 mm may simulate the user's perception of natural light filtered through a canopy of foliage.

Figure 2:
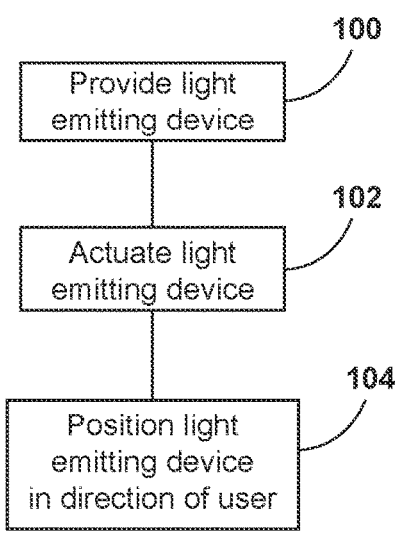
FIG. 2 is a schematic flow chart of a method for treating a neurological disorder.

As best illustrated in FIG. 2, a method for utilizing the ocular light therapy arrangement may include providing the light emitting device 100, namely, the light bulb 10, actuating the light bulb 10 such that the light emitted from the light bulb 10 has the characteristics and is within the parameters as described above, and positioning the light bulb 10 such that the light emitted from the light bulb 10 illuminates a space occupied by the user, such that the light is preferably received by the eyes of a user, thereby reducing stimulation of the user's retina and brain cortex and reducing and/or soothing or preventing the triggering of neurological disorder symptoms typically associated with the neurological disorders such as pain, and as discussed above.

The present inventive ocular light therapy arrangement and method is effective for treating users having a neurological disorder, and in particular to reducing the neurological disorder symptoms such as headaches and pain, nausea, vomiting and extreme sensitivity to light and sound, typically associated with neurological disorders such as migraines, fibromyalgia, neuropathy, chronic headaches, and the like, and provides a relatively low cost treatment for such disorders eliminating or reducing the necessity for medications and, in turn, side effects typically associated with such drugs and medications, eliminating or reducing the necessity for invasive procedures and the side effects and serious risk factors associated therewith, and is particularly well adapted for the proposed use. As a result, the present inventive arrangement and related method may allow the user to resume or conduct normal indoor life/work functions and activities without having to seek refuge and/or recovery in a separate dark or dimly lit room.

In the foregoing description, it will be readily appreciated by those skilled in the art that alternative embodiments of the various components and elements of the disclosed embodiments and modifications to the invention may be made without departing from the concepts disclosed herein. Such modifications are to be considered as included in the following claims, unless these claims by their language expressly state otherwise.

The invention claimed is:

1. An ocular light therapy arrangement for treating a user having a neurologic disorder, comprising:
a light emitting device that emits a light having a flicker rate of less than or equal to about 2 Hz and/or greater than or equal to about 85,000 Hz only at a first wavelength of within a first range of from about 500 nm to about 565 nm and at a second wavelength of within a second range of from about 800 nm to about 1 mm, such that the light has a targeted perception of flicker to mimic natural light through a canopy of foliage and is effective to reduce neurologic disorder symptoms by reducing stimulation of the user's retina and brain cortex, wherein the light has less than or equal to about 2.5% flicker within the first wavelength range of within the first range of from about 500 nm to about 565 nm.

2. The ocular light therapy arrangement of claim 1, wherein the first range is between 500 nm and 565 nm.

3. The ocular light therapy arrangement of claim 2, wherein the first range is between 510 nm and 550 nm.

4. The ocular light therapy arrangement of claim 3, wherein the wavelength is about 525 nm.

5. The ocular light therapy arrangement of claim 4, wherein the flicker rate is zero Hz.

6. The ocular light therapy arrangement of claim 1, wherein the light emitting device comprises a light emitting diode.

7. The ocular light therapy arrangement of claim 1, wherein the light emitting device is configured to have an output of between about 1 lumen and about 1000 lumen.

8. The ocular light therapy arrangement of claim 7, wherein the output of the light emitting device is variable between about 300 lumen and about 600 lumen.

9. The ocular light therapy arrangement of claim 1, wherein the light emitting device is configured to have an output of greater than or equal to about 600 lumen.

10. The ocular light therapy arrangement of claim 1, further comprising:
a base member configured to be releasably received within a light bulb socket;
a housing member coupled to the base member; and a diffuser coupled to the base member and cooperating with the base member to define an interior space, wherein the light emitting device is located within the interior space.

11. The ocular light therapy arrangement of claim 1, wherein the second range is between about 710 nm and about 850 nm.

12. The ocular light therapy arrangement of claim 1, wherein the neurologic disorder symptoms include neurologic disorder symptoms of a migraine.

13. A method for treating a neurological disorder of a user with an ocular light therapy arrangement, comprising:
   providing a light emitting device;
   actuating the light emitting device such that the light emitting device produces a light having a flicker rate of less than or equal to about 2 Hz and/or greater than or equal to about 85,000 Hz only at a first wavelength of within a first range of from about 500 nm to about 565 nm and at a second wavelength of within a second wavelength range of from about 800 nm to about 1 mm, wherein the light has less than or equal to about 2.5% flicker within the first wavelength range of within the first range of from about 500 nm to about 565 nm, such that the light has a targeted perception of flicker to mimic natural light through a canopy of foliage; and
   positioning the light emitting device such that the light emitted from the light emitting device illuminates a space occupied by the user, wherein the light is effective to reduce neurologic disorder symptoms by reducing stimulation of the user's retina and brain cortex.

14. The method of claim 13, where the first range is between 500 nm and 565 nm.

15. The method of claim 13, wherein the flicker rate is less than or equal to about 1 Hz.

16. The method of claim 13, wherein this second range is between about 710 nm and 850 nm.

17. An ocular light therapy arrangement for treating a user having a neurologic disorder, comprising:
   a light emitting device that emits a light having a flicker index of less than or equal to about 1.0 at a first wavelength of within a first range of from about 500 nm to about 565 nm and at a second wavelength of within a second range of from about 800 nm to about 1 mm, such that the light has a targeted perception of flicker to mimic natural light through a canopy of foliage and is effective to reduce neurologic disorder symptoms by reducing stimulation of the user's retina and brain cortex, wherein the light has less than or equal to about 2.5% flicker within the first wavelength range of within the first range of from about 500 nm to about 565 nm.

18. The ocular light therapy arrangement of claim 17, wherein the light has a flicker rate of less than or equal to about 2 Hz within the wavelength range of from about 500 nm to about 565 nm.

19. The ocular light therapy arrangement of claim 17, wherein the light emitting device only emits the light with a wavelength range of between about 480 nm and about 600 nm.

20. The ocular light therapy arrangement of claim 17, wherein the light emitting device is configured to have an output of between about 300 lumen and about 600 lumen.

21. The ocular light therapy arrangement of claim 19, further comprising:
   a base member configured to be releasably received within a light bulb socket;
   a housing member coupled to the base member; and
   a diffuser coupled to the base member and cooperating with the base member to define an interior space, wherein the light emitting device is located within the interior space.

* * * * *

UNITED STATES PATENT AND TRADEMARK OFFICE
CERTIFICATE OF CORRECTION

| | |
|---|---|
| PATENT NO. | : 12,005,268 B2 |
| APPLICATION NO. | : 17/303318 |
| DATED | : June 11, 2024 |
| INVENTOR(S) | : David S. MacKenzie |

It is certified that error appears in the above-identified patent and that said Letters Patent is hereby corrected as shown below:

On the Title Page

Item (57) Abstract, Lines 2, and 7:
"neurologic" should be — neurological —

Item (57) Abstract, Line 3:
"the" should be — that —

In the Specification

Column 1, Lines 27, and 33:
"neurologic" should be — neurological —

Column 1, Line 46:
"neurologic" should be — neurological —

Column 1, Lines 51, and 56:
"neurologic" should be — neurological —

Column 1, Line 56:
"neurologic" should be — neurological —

Column 3, Line 8 (first occurrence):
After "to" insert -- or --

Column 3, Line 46:
"nm" should be — mm —

Signed and Sealed this
Fifth Day of November, 2024

Katherine Kelly Vidal
*Director of the United States Patent and Trademark Office*

CERTIFICATE OF CORRECTION (continued)
U.S. Pat. No. 12,005,268 B2

In the Claims

Column 4, Claim 1, Lines 29, and 38:
"neurologic" should be — neurological —

Column 5, Claim 12, Lines 9, and 10:
"neurologic" should be — neurological —

Column 5, Claim 13, Line 29:
"neurologic" should be — neurological —

Column 5, Claim 14, Line 31:
"where" should be — wherein —

Column 5, Claim 16, Line 37:
"this" should be — the —

Column 6, Claim 17, Lines 2, and 10:
"neurologic" should be — neurological —